United States Patent [19]
Boudewijn et al.

[11] Patent Number: 5,453,088
[45] Date of Patent: Sep. 26, 1995

[54] HYDRODYNAMIC SUCTION CATHETER

[75] Inventors: Alexander C. Boudewijn, Leek; Jan Weber, Roden, both of Netherlands

[73] Assignee: Cordis Corporation, Miami Lakes, Fla.

[21] Appl. No.: 227,361

[22] Filed: Apr. 13, 1994

[30] Foreign Application Priority Data

Apr. 13, 1993 [NL] Netherlands ............... 9300626

[51] Int. Cl.⁶ ............... A61M 3/00; A61M 1/00
[52] U.S. Cl. ............... 604/43; 604/35; 606/159
[58] Field of Search ............... 604/35, 39, 41–44, 604/52, 53, 131, 150; 606/159

[56] References Cited

U.S. PATENT DOCUMENTS

| | | |
|---|---|---|
| 2,568,566 | 5/1946 | Sokolik . |
| 4,715,848 | 12/1987 | Beroza ............... 604/35 |
| 4,790,818 | 12/1988 | De Luca . |
| 5,037,432 | 8/1991 | Molinari ............... 604/35 |
| 5,259,842 | 11/1993 | Plechinger et al. ............... 604/43 |
| 5,318,518 | 6/1994 | Plechinger et al. ............... 604/35 |
| 5,320,599 | 6/1994 | Griep et al. ............... 604/43 |

FOREIGN PATENT DOCUMENTS

| | | | |
|---|---|---|---|
| 0175096 | 3/1986 | European Pat. Off. ............... 604/35 |
| 0442579 | 8/1991 | European Pat. Off. . |
| 9215343 | 9/1992 | WIPO . |

*Primary Examiner*—C. Fred Rosenbaum
*Assistant Examiner*—Frank Wilkens, III
*Attorney, Agent, or Firm*—Thomas R. Vigil

[57] ABSTRACT

The drainage catheter comprises a basic tubular body having a distal end, a proximal end, a pressure channel in the tubular body and a discharge channel in the tubular body, the distal end having a bending of the pressure channel to communicate with the discharge channel. A nozzle ejector formation is provided in the distal end of the catheter after the bend in the pressure channel and having an orifice facing proximally into the discharge channel. The distal end further has an inlet opening disposed adjacent the orifice of the nozzle ejector formation. The basic tubular body has, at the proximal end, a pressure inlet to the pressure channel and a discharge outlet from the discharge channel. Coupling structure is coupled to the proximal end of the basic tubular body and includes a first, pressure channel for coupling a source of fluid under pressure to the pressure inlet at the proximal end of the catheter tubular body, a second, discharge channel for coupling the discharge outlet at the proximal end of the tubular body to a reservoir, and a third, curved channel for coupling, at the pressure inlet, the source of fluid under pressure to, at the discharge outlet, the reservoir, whereby fluid under pressure flowing through the third channel creates a suction at the discharge outlet to educe fluid from the discharge channel to the reservoir.

9 Claims, 3 Drawing Sheets

HYDRODYNAMIC SUCTION CATHETER

FIELD OF THE INVENTION

The invention relates to a hydrodynamic drainage catheter comprising a basic body with a distal and a proximal end in which a pressure channel and a discharge channel have been formed. At the distal end the discharge channel is connected to a suction opening and the pressure channel to a jet nozzle which empties into the discharge channel and is directed towards the proximal end of the catheter.

Description of the realed art including information disclosed under 37 CRF 1.97–1.99.

A prior art drainage catheter is known from the European patent application 0 442 579, wherein the inlet opening has been formed in a side wall of the discharge channel and the jet nozzle ends adjacent to the distal end of this opening and is directed closely along it. Together with the inlet opening, the jet nozzle forms an ejector. When liquid under pressure is supplied to the jet nozzle via the pressure channel, the liquid jet flowing from the jet nozzle and directed along the opening will generate a suction this opening. An important application of such a catheter is therefore a thrombectomy-catheter for the removal of blood clots or thrombi from the vascular system of a patient.

When such catheters are very long and thin, removal of the sucked up material through and from the discharge channel can become difficult. The flow resistance in the discharge channel becomes too great in order to maintain sufficient flow in this channel with the aid of the liquid jet from the jet nozzle.

SUMMARY OF THE INVENTION

The object of the invention is to improve a hydrodynamic suction catheter of the type described in the preamble in such a way that also at a greater length and smaller diameter its function will remain reliable.

According to the invention there is provided a drainage catheter comprising a basic tubular body having a distal end, a proximal end, a pressure channel in the tubular body and a discharge channel in the tubular body, the distal end having a bending of the pressure channel to communicate with the discharge channel, a nozzle ejector formation in the distal end of the catheter after the bend in the pressure channel and having an orifice facing proximally into the discharge channel, the distal end further having an inlet opening disposed adjacent the orifice of the nozzle ejector formation, the basic tubular body having, at the proximal end, a pressure inlet to the pressure channel and a discharge outlet from the discharge channel, coupling structure coupled to the proximal end of the basic tubular body and including a first, pressure channel for coupling a source of fluid under pressure to the pressure inlet at the proximal end of the catheter tubular body, a second, discharge channel for coupling the discharge outlet at the proximal end of the tubular body to a reservoir, and a third, curved channel for coupling, at the pressure inlet, the source of fluid under pressure to, at the discharge outlet, the reservoir, whereby fluid under pressure flowing through the third channel creates a suction at the discharge outlet to educe fluid from the discharge channel to the reservoir. Herewith it is possible to utilize the liquid under pressure already present to generate additional suction with the aid of the liquid jet pump. Because of the extra suction the sucked up material can still be removed in a reliable way through a discharge channel of the catheter with a greater length and a smaller diameter. The advantage of the known catheter that no suction sources dependent on other sources of energy need to be used, remains unchanged with the catheter according to the invention.

An advantageous development of the catheter according to the invention. Connecting the catheter according to the invention becomes consequently very easy.

The provision of a Y piece having an inlet from a jet pump to one channel that goes through the Y piece to the pressure channel and also having such inlet connected to a generally U-shaped channel that has an outlet that communicates generally in line with a discharge channel and faces proximally, enables pressure to be supplied to the pressure channel and suction to be applied to the discharge channel with one liquid jet pump. As a result, a compact liquid jet pump can be made so that the embodiment of this catheter is easy to handle. The Y-piece is preferably made by injection moulding. The liquid jet pump and the connecting channels can in that case be defined by an insert consisting of two parts joined by for instance ultrasonic welding to make up a whole.

In order not to affect the working of the jet nozzle adversely the flow resistance for the pressurized liquid from the jet pump is established to be greater than the flow resistance in the discharge channel is preferably applied.

The invention will be explained in greater detail in the following description with reference to the attached drawings.

DETAILED DESCRIPTION OF THE PREFERRED EMBODIMENT

Figure 1:
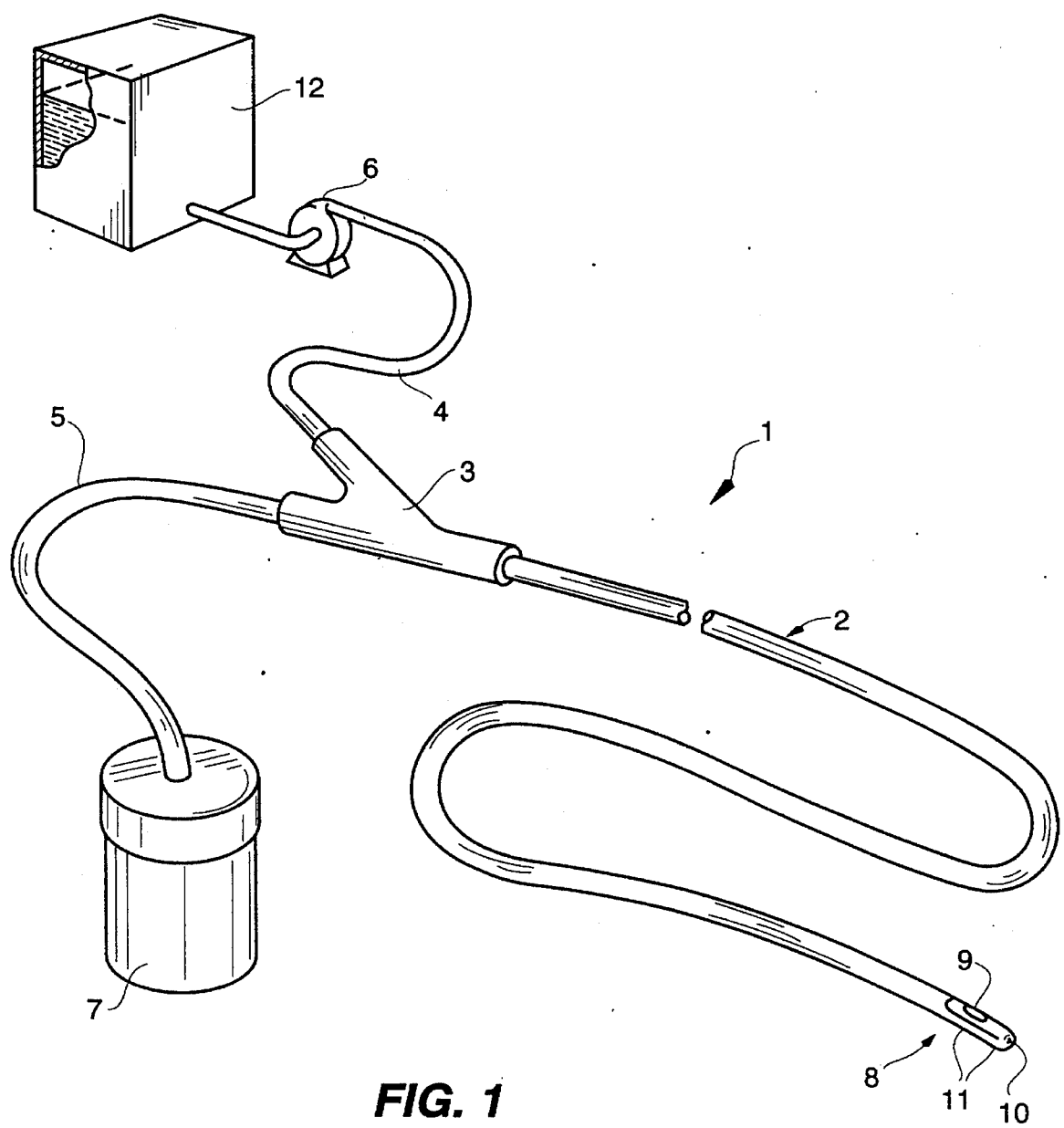
FIG. 1 is a schematic view of a catheter according to the invention in the position of use.
Figure 4:
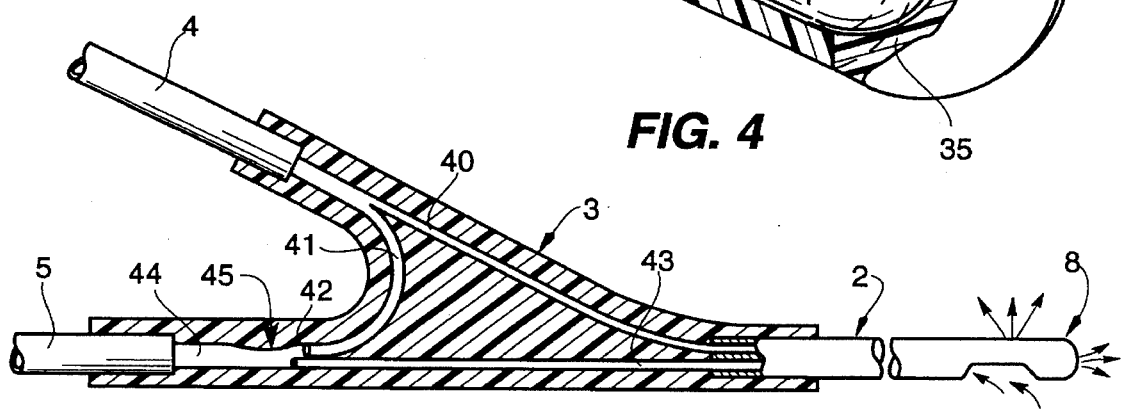
FIG. 4 represents a partly cross-sectional view of another embodiment of a catheter.
Figure 5:
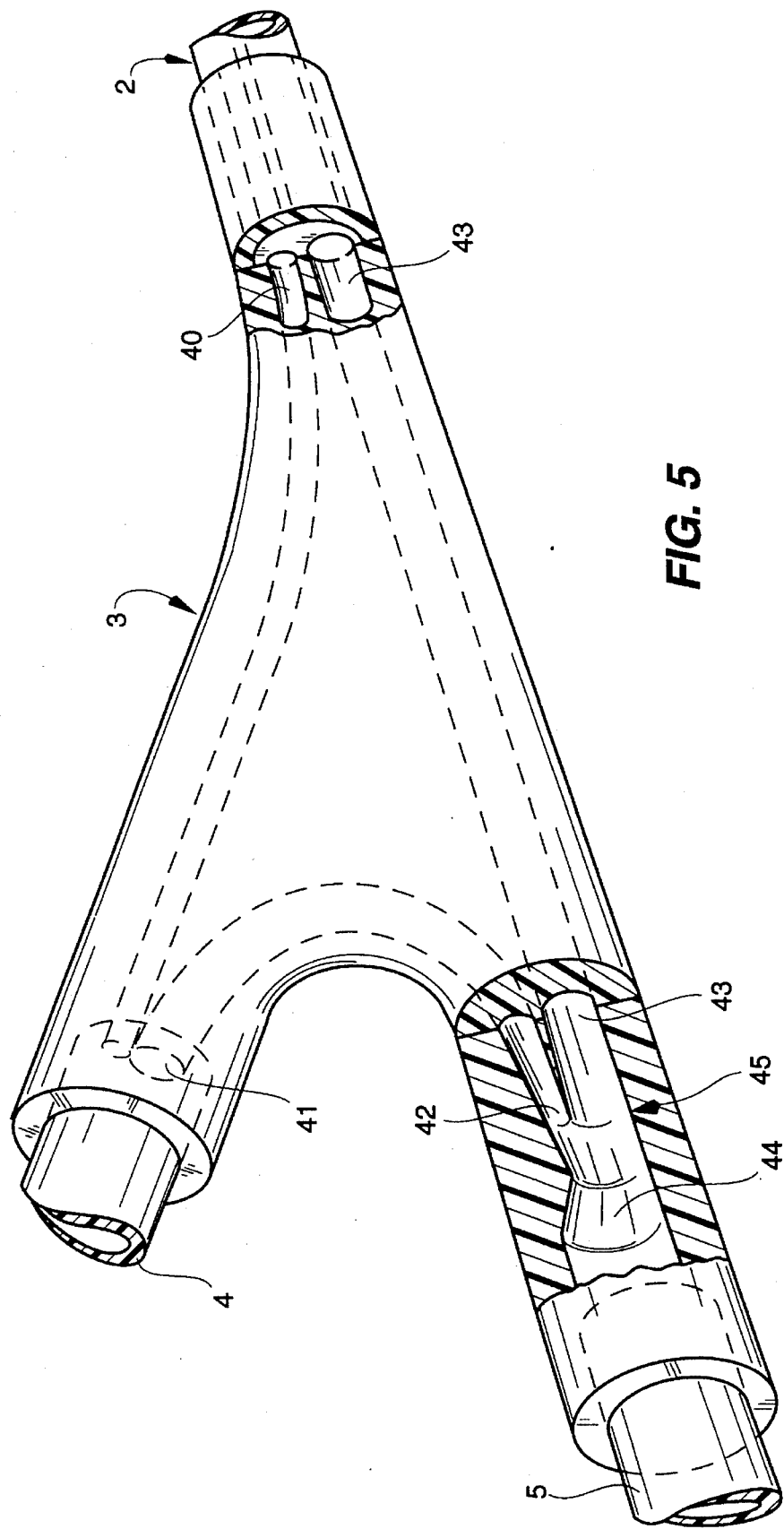
FIG. 5 represents the Y-piece of the catheter of FIG. 4 enlarged and in a partly broken away perspective view.

A preferred embodiment of the catheter 1 as shown in FIG. 1 comprises a tube-like basic body 2 with a distal end 8 in which a suction opening 9 has been formed. Close to the other, proximal end the basic body 2 is connected to a Y-piece 3 which is shown in greater detail in FIG. 4 and 5 and which will be explained further with reference to these drawings.

Connected with the Y-piece 3 is a first tube 4 to which a source of liquid under pressure, in this case a pump 6, is connected to and draws liquid from a reservoir 12. Furthermore a discharge tube 5 is connected to the Y-piece 3 leading to a discharge reservoir 7.

The pressure line 4 is, inside the Y-piece 3, connected with a pressure channel in the basic body 2 and also with a pressure inlet of a liquid jet pump incorporated in the Y-piece 3.

Figure 2:
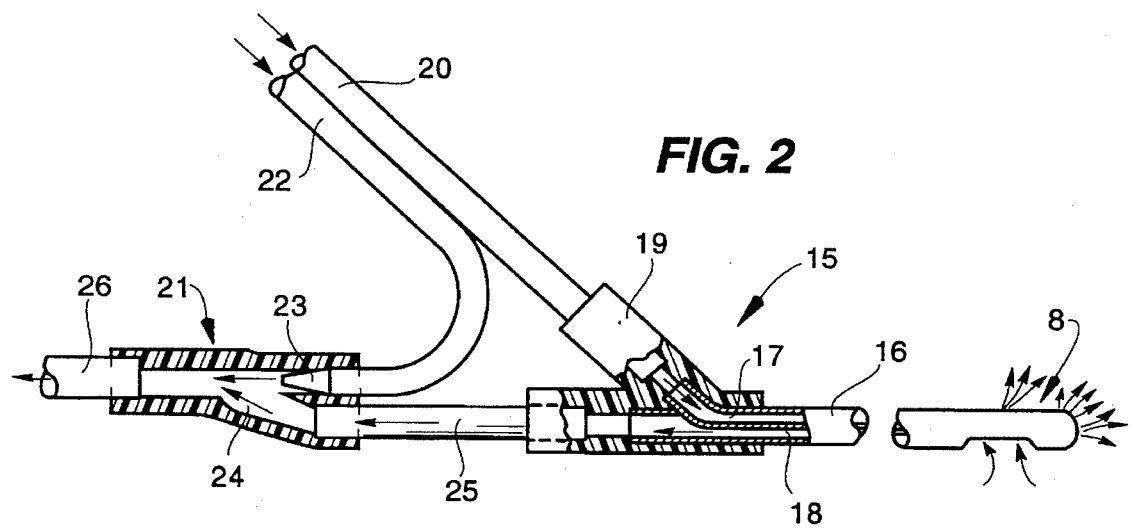
FIG. 2 represents a partly broken away view of an embodiment of a catheter according to the invention.

The working of the catheter as shown in FIG. 1 will be explained further with reference to FIG. 2 and 3. In FIG. 2 it can be seen that the basic body 16 of the illustrated catheter 15 comprises a pressure channel 17 and a discharge channel 18. This basic body 16 has been incorporated in a distribution piece 19 in which the two channels 17, 18 of the basic body are connected to separate inlets and outlets respectively. The inlet leading to pressure channel 17 is connected to a tube 20 delivering the liquid under pressure, for example in the way shown in FIG. 1 with the aid of a pump.

Figure 3:
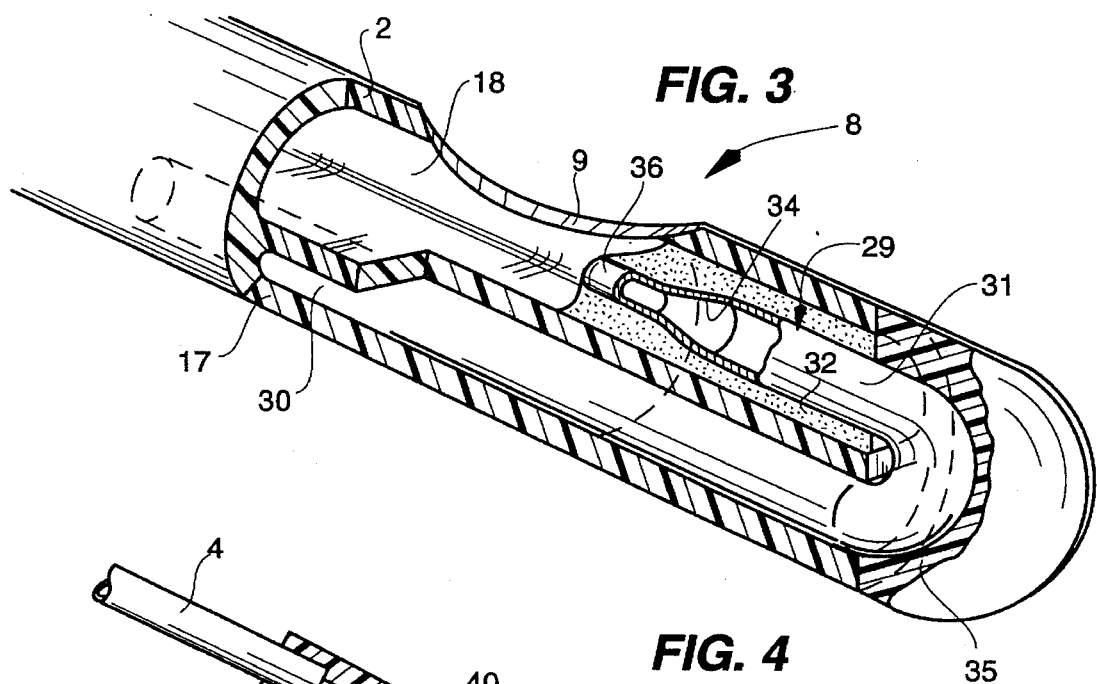
FIG. 3 represents an enlarged, partly broken away view of the distal end of a catheter according to the invention.

The liquid under pressure flows via pressure channel 17 in the basic body 16 to the distal end 8 of the catheter as shown in FIG. 3.

A U-shaped metal tube 29 is, as shown in FIG. positioned with its legs 30, 31 in the pressure channel 17 and the discharge channel 18 respectively. The U-tube is fixed in position by hardened filling material 32. The end of the catheter is finished with a nosepiece 35 made of a soft plastic material. The end portion has been ground in the usual manner in order to ensure a smooth surface.

The leg 31 of the U-shaped metal tube extending into the discharge channel is provided with a tapered portion 34, so that a jet nozzle 36 is formed at the end of the leg 31. This jet nozzle 36 directs the fluid which is delivered through the pressure channel 17 in a carefully controlled manner along the inside of the inlet opening 9, so that an ejector action is obtained in a reliable and efficient way. By means of this ejector action material outside the catheter in the vicinity of the opening 9 is sucked through this opening 9 and is carried along in the discharge channel 18 towards the proximal end. As is shown in FIG. 2 a tube 25 connects to the discharge channel 18 inside the distribution piece 19. This tube 25 is connected to the suction inlet 24 of a liquid jet pump 21. The liquid jet pump 21 also comprises a pressure inlet to which a pressure tube 22 is connected which, inside the liquid jet pump 21, debouches into a jet nozzle 23. Liquid under pressure delivered through the tube 22 is emitted in the form of a jet at a relatively high velocity through the jet nozzle 23, thus creating suction at the location of suction inlet 24. The removal of material sucked up through inlet opening 9 via the discharge channel 18 and the tube 25 is supported by means of this suction. Together with the liquid delivered through the pressure line 22 the sucked up material is removed through the tube 26 to a discharge reservoir such as the discharge reservoir 7 of FIG. 1.

As stated before, in the preferred embodiment of FIG. 1, the liquid jet pump is incorporated in the Y-piece 3.

In this embodiment the pressure connection of the pressure channel of the catheter has furthermore been combined with the pressure inlet of the liquid jet pump to form one pressure line 4. In the Y-piece 3 two connecting channels 40 and 41, also formed in the Y-piece 3, branch off from the pressure line 4. The connecting channel 40 leads to the pressure channel of the basic body of the catheter and the connecting channel 41 leads to the nozzle 42 of the liquid jet pump. A third connecting channel 43 leads from the discharge channel of the body of the catheter 2 to the suction inlet of the pump 45. The discharge channel 44 of the pump 45 is connected to the discharge tube 5 of the Y-piece 3.

As appears clearly from the figures, the catheter according to the invention with the combined pressure connection for the pressure channel and pressure inlet for the liquid jet pump, is just as easy to use as the previously known hydrodynamic suction catheter. Compared with the known catheter there are no additional connections while the catheter according to the invention can be manufactured with a greater length and a smaller diameter.

The Y-piece 3 can for instance be manufactured by injection moulding whereby the liquid jet pump is defined in the insert in the usual or obvious manner. This insert itself can be made in two halves by injection moulding, which halves will be joined afterwards by for instance ultrasonic welding to form one unit. The basic body of the catheter and the connecting tubes can be fixed in the Y-piece 3 by welding, glueing or by injection moulding of the Y-piece.

As the catheter according to the invention can create the suction required for the removal of unwanted material in two places, namely at the inlet opening at the distal end by ejector action and in the liquid jet pump, there is considerable freedom of design, especially where the distal end of the catheter is concerned.

When an embodiment, chosen for particular reasons, would result in a somewhat diminished ejector action, this reduced ejector action could be compensated for by manufacturing the liquid jet pump in such a way that it creates a stronger suction. It is even possible that the liquid jet pump is the only element creating suction and that the jet nozzle at the distal end serves for instance only as a means to pulverize the material to be sucked away.

We claim:

1. A drainage catheter comprising a basic tubular body having a distal end, a proximal end, a pressure channel in said tubular body and a discharge channel in said tubular body, said distal end having a bending of said pressure channel to communicate with said discharge channel, a nozzle ejector formation in said distal end of said catheter after said bend in said pressure channel and having an orifice facing proximally into said discharge channel, said distal end further having an inlet opening disposed adjacent said orifice of said nozzle ejector formation, said basic tubular body having, at said proximal end, a pressure inlet to said pressure channel and a discharge outlet from said discharge channel, coupling means coupled to said proximal end of said basic tubular body and including a first, pressure channel for coupling a source of fluid under pressure to said pressure inlet at said proximal end of said catheter tubular body, a second, discharge channel for coupling said discharge outlet at said proximal end of said tubular body to a reservoir, and a third, curved channel for coupling, at said pressure inlet, the source of fluid under pressure to, at said discharge outlet, the reservoir, whereby fluid under pressure flowing through said third channel creates a suction at said discharge outlet to educe fluid from said discharge channel to the reservoir.

2. The catheter of claim 1 wherein said third channel curves in a generally U-shaped path from said pressure inlet in said coupling means to said discharge outlet of said second discharge channel from said coupling means.

3. The catheter of claim 1 wherein a tubing from the source of fluid under pressure is coupled, at said pressure inlet of said coupling means to both said first, pressure channel and to said third channel.

4. The catheter of claim 1 wherein said coupling means is a generally Y-shaped piece having said third channel therein as well as said first, pressure channel and said second, discharge channel.

5. The catheter of claim 1 wherein said coupling means is an injection molded Y-shaped piece having formed therein said first, pressure channel, said second, discharge channel and said third channel.

6. The catheter of claim 1 wherein said first, pressure channel in said coupling means is constructed to provide greater resistance to the flow of fluid therethrough than is said second, discharge channel.

7. The catheter of claim 1 wherein said first, pressure channel in said coupling means has a smaller cross-section than the cross-section of said second, discharge channel in said coupling means.

8. The catheter of claim 1 wherein said first, pressure channel in said coupling means has a smaller cross-section than the cross-section of said second, discharge channel in said coupling means and wherein said third channel has a larger cross-section than the cross-section of said first, pressure channel and has an outlet end which tapers to a smaller cross-section channel thereby to establish an ejector nozzle formation with an orifice facing proximally toward the reservoir thereby to create a suction away from said discharge outlet from said second, discharge channel in said coupling means.

9. The catheter of claim 8 wherein the cross-section of said discharge outlet of said discharge channel from said coupling means is larger than the cross-section of said discharge channel from an inlet thereof to said ejector nozzle formation.

* * * * *